United States Patent [19]
Giefer

[11] Patent Number: 4,748,992
[45] Date of Patent: Jun. 7, 1988

[54] CONTACT LENS DISINFECTION

[75] Inventor: Günter Giefer, Heusenstamm, Fed. Rep. of Germany

[73] Assignee: Ciba Vision Care Corporation, Atlanta, Ga.

[21] Appl. No.: 836,804

[22] Filed: Mar. 6, 1986

Related U.S. Application Data

[62] Division of Ser. No. 451,562, Dec. 20, 1982, Pat. No. 4,585,488.

[30] Foreign Application Priority Data

Dec. 21, 1981 [DE]  Fed. Rep. of Germany ....... 1350638

[51] Int. Cl.$^4$ .............................................. B08B 3/08
[52] U.S. Cl. ......................................... 134/84; 134/94; 252/106; 422/301
[58] Field of Search ............................ 134/30, 27, 84; 252/89.1, 106, 173, 543, DIG. 10, 188.2; 424/127; 422/30; 435/78

[56] References Cited

U.S. PATENT DOCUMENTS

| | | | |
|---|---|---|---|
| 3,954,644 | 5/1976 | Krezanoski et al. | 252/106 |
| 4,127,423 | 11/1978 | Rankin | 134/26 X |
| 4,164,477 | 8/1979 | Whitley | 252/106 X |
| 4,305,905 | 12/1981 | Gallin | 424/127 |
| 4,395,346 | 7/1983 | Kleist | 252/106 X |
| 4,438,011 | 3/1984 | Howes | 252/106 |
| 4,521,375 | 6/1985 | Houlsby | 206/5.1 |

*Primary Examiner*—Harvey C. Hornsby
*Assistant Examiner*—Frankie L. Stinson
*Attorney, Agent, or Firm*—Brumbaugh, Graves, Donohue & Raymond

[57] ABSTRACT

A system for disinfecting and cleaning hygienic articles, particularly contact lenses for the human eye, in which, during a first time span, a first container contains hydrogen peroxide solution which acts onto the hygienic article and subsequently, during a second time span, the hydrogen peroxide which adheres to the hygienic article is split up into water and oxygen under the action of a catalyst either in the first container or in a second container containing the catalyst. According to the invention, catalase is used as the catalyst. Through this, the speed and thoroughness of the removal of hydrogen peroxide residues after the disinfecting phase are substantially increased.

4 Claims, 1 Drawing Sheet

CONTACT LENS DISINFECTION

This application is a division of application Ser. No. 451,562, filed on Dec. 20, 1982 and now U.S. Pat. No. 4,585,488.

FIELD OF THE INVENTION

This invention relates to disinfection of contact lenses, particularly contact lenses for the human eye.

BACKGROUND OF THE INVENTION

During the use of contact lenses, the lenses become contaminated and the accumulation of pathogenic germs must not be permitted to exceed a critical limit in order to avoid the danger of an infection of the eye. For this reason, a daily disinfection of contact lenses is necessary. This is particularly true for hydrophilic soft lenses, which are used widely today.

For this purpose, a method is known which utilizes hydrogen peroxide, which has both an oxidizing, germ-killing, cleaning effect and a smell-killing effect. In this method, the contact lenses are first exposed to the action of a 3 to 30 percent solution of hydrogen peroxide, which can for example take place in a small container in which the contact lenses are arranged in a carrying basket. The time period during which the hydrogen peroxide must act onto the contact lenses in order to achieve a sufficient disinfection and cleaning is approximately 20 minutes. The hydrogen peroxide which adheres to the contact lenses must subsequently be removed, and in the known method this is done by moving the contact lenses into a second container which contains a neutral liquid and a catalyst, in the presence of which catalyst the hydrogen peroxide is split up into water and oxygen according to the formula:

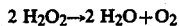

$$2 H_2O_2 \rightarrow 2 H_2O + O_2$$

The catalyst is a metal-coated solid body.

A disadvantage of the conventional method is that the second method step, namely the eliminating of the hydrogen peroxide by splitting it up, takes a relatively long time. At least four hours are needed for this. If, for example, a user of contact lenses forgets in the evening to change the contact lenses from the hydrogen peroxide solution to the solution containing the catalyst, there is usually insufficient time the next morning to remove the hydrogen peroxide residues from the contact lenses and thereby avoid a burning sensation in the eyes during wearing of the contact lenses. According to a modification of the known method, the metallic cayalyst is already present in the hydrogen peroxide solution during the time when the hydrogen peroxide solution acts onto the contact lenses. Thus, the disinfecting and cleaning operation of the contact lenses and the decomposition of the hydrogen peroxide by the catalyst start at the same time. This is possible in this known method, since the decomposition which is effected by the catalyst takes place slowly. This one-step method also has the important disadvantage that it is very slow (it takes several hours). Moreover, in this known method, remaining residues of hydrogen peroxide are thereafter removed by a final washing in a salt solution.

A basic purpose of the invention is to improve the method mentioned above so that the time span required for the second method step is substantially reduced and at the same time a very high-grade removal of the hydrogen peroxide is achieved.

According to one aspect of the invention, a contact lens disinfection system is provided including a container containing an aqueous hydrogen peroxide disinfection solution for disinfecting a contact lens together with a container containing an aqueous isotonic solution of disolved catalase sufficient to decompose the hydrogen peroxide adhering to the contact lens after disinfection and render the lens suitable for wearing.

Another aspect of the invention is directed to the combination of a disinfected contact lens having adherent residual hydrogen peroxide and an isotonic catalase solution in contact with the lens.

DESCRIPTION OF PREFERRED EMBODIMENTS

Catalase is an enzyme which is preferably obtained from beef liver and has a crystalline structure. It can be obtained on the market as a highly concentrated solution dissolved in 30% glycerin and 10% ethanol and is used in the grocery industry, in particular in the treatment of milk.

The invention is based on the recognition that the removal of hydrogen peroxide residues from the hygienic articles in the presence of catalase as catalyst takes place substantially more quickly and thoroughly than when conventional catalysts are used. In the method according to the invention, the time span for the second method step takes only a few minutes (approximately 5 minutes). In the method according to the invention, it is thus not important if a user of contact lenses forgets in the evening to start the second method step, since taking care of it the next morning requires only a few minutes. Through the very turbulent decomposition of the hydrogen peroxide, not only is the necessary treatment time substantially shortened, but since the catalyst which is added in solution also reaches the hydrogen peroxide which has penetrated the contact lense material, an explosionlike decomposition takes place which breaks off contamination from the surface of the contact lenses, which contamination has become brittle during the first method step. The removal of hydrogen peroxide residues with the inventive method is so thorough that a subsequent washing of the lenses in a salt solution is not needed.

In using the organic catalase, there exists a practical problem that it is not very stable and storing it is difficult. The above-mentioned highly concentrated catalase solution, which can be obtained in commerce, must be stored at 4° C. and even then can be stored only for several months. According to the invention, the catalase for carrying out the inventive method can be stored in sodium chloride solution, in which it has surprisingly been found to be capable of storage for a very long time with minimal temperature susceptibility. The stability of the catalase in this form makes the method according to the invention extremely well suited for practical use. For this purpose, a volume part of catalase in the above-mentioned commercially available form is added to approximately 100 to 1000 volume parts, preferably 400 to 600 volume parts, of an approximately 0.8 to 1.0% sodium chloride solution.

Figure 1:
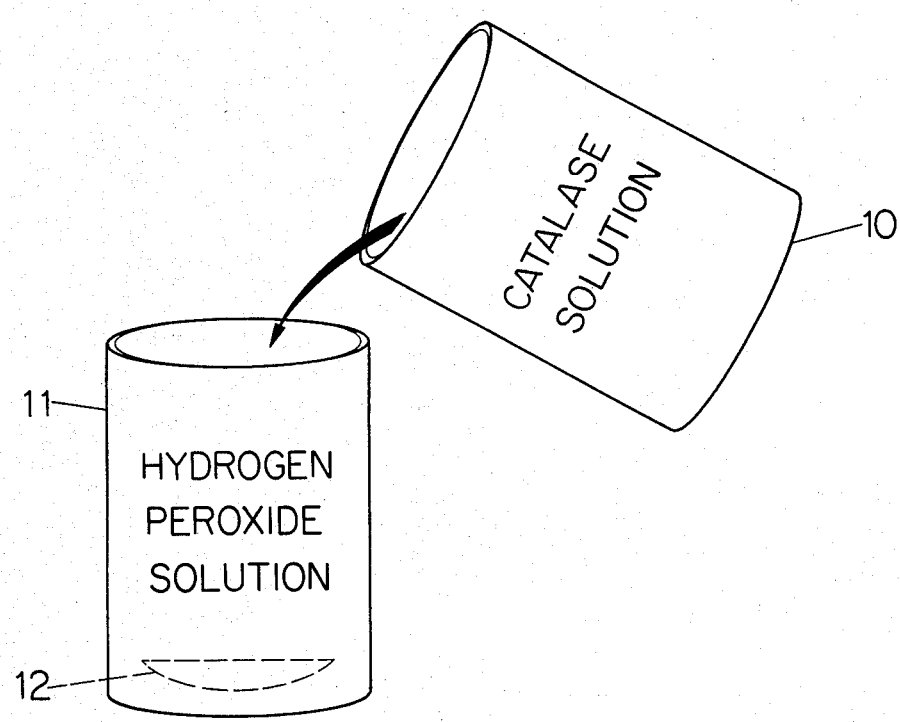
FIG. 1 is a schematic illustration showing a contact lens disinfection system in accordance with the invention in which catalase solution from the catalase container is added to the hydrogen peroxide solution container containing a contact lens.
Figure 2:
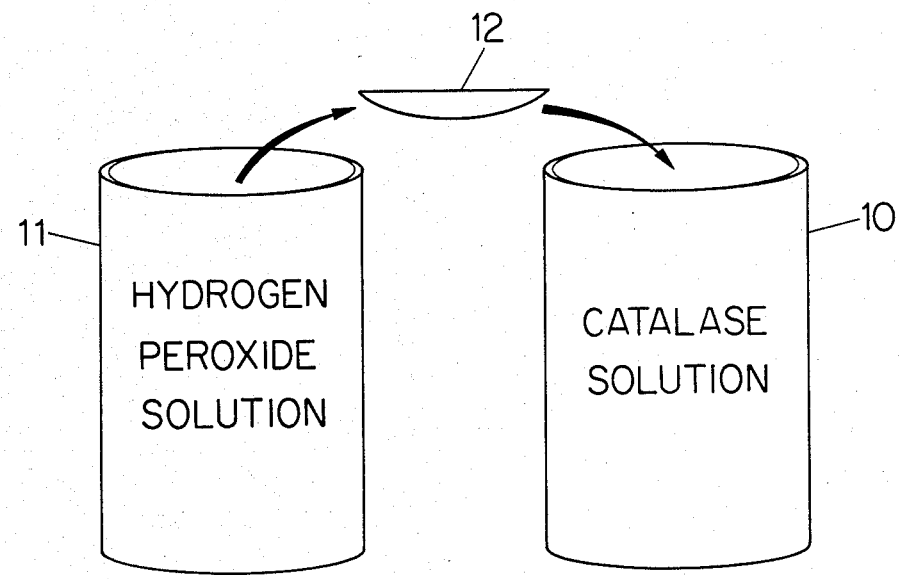
FIG. 2 is a schematic illustration of another embodiment of a contact lens disinfection system in accordance with the invention in which a contact lens is transferred from a container containing a hydrogen peroxide solution to a container containing a catalase solution.

The decomposition step can be carried out in various ways. At the end of the disinfection time, catalase in the form of tablets or a highly concentrated solution from a container 10 can be added directly to a treatment container 11 containing a lens 12 and a hydrogen peroxide solution as shown in FIG. 1. An alternative approach involves replacing the hydrogen peroxide solution in the container 11 with a neutral liquid, for example, a sodium chloride solution, to which is then added a somewhat highly concentrated catalase solution from the container 10 or tablets containing catalase. One can best use, as the liquid which replaces the hydrogen peroxide solution in the container 11, the above-mentioned liquid which consists of highly concentrated catalase stored in a sodium chloride solution. It is also possible to work with two containers in the manner shown in FIG. 2, wherein one container 11 contains the hydrogen peroxide solution and the other container 10 contains the neutral liquid with the catalase to which the lens 12 is transferred from the container 11 after treatment. Particularly during the treatment of contact lenses 12, a sodium chloride solution is preferably used as the neutral liquid for the second method step, the concentration of which corresponds to the concentration of eye fluid (i.e., isotonic).

For practicality in carrying out the inventive method, it is also conceivable to press the catalase in a crystalline form, with a suitable highly water-soluble base material, into tablets. For the base material, commercially available substances can be used. These tablets then replace the above-mentioned highly concentrated catalase solution.

Other hygienic articles which can be treated according to the inventive method include, for example, dental protheses or the ear inserts of hearing aids.

The concentration in which the catalase is added, in its commercially available form, to the base liquid, for example the hydrogen peroxide solution or the sodium chloride solution, can vary in a wide range from approximately 0.1 to 1 percent by volume.

I claim:

1. A contact lens disinfection system comprising:
   (a) a container containing an aqueous hydrogen peroxide disinfection solution for disinfecting a contact lens; and
   (b) a container containing an aqueous isotonic solution of a hydrogen peroxide decomposition catalyst comprising dissolved catalase in a concentration sufficient to decompose hydrogen peroxide adhering to said contact lens after disinfection by application of the aqueous isotonic solution to the lens and thereby render the lens suitable for wearing.

2. A contact lens disinfection system according to claim 1 wherein said aqueous isotonic solution contains about 0.8 to 1.0% sodium chloride.

3. In combination, a contact lens with adherent hydrogen peroxide retained following disinfection by immersion of the lens in a hydrogen peroxide solution, and an isotonic solution of a hydrogen peroxide decomposition catalyst comprising catalase in contact therewith, the isotonic catalase solution having a catalase concentration sufficient to decompose the retained hydrogen peroxide.

4. The combination of claim 3 wherein said aqueous isotonic catalase solution contains about 0.8 to 1.0% sodium chloride.

* * * * *